US00PP25455P3

(12) United States Plant Patent
Vinson

(10) Patent No.: US PP25,455 P3
(45) Date of Patent: Apr. 21, 2015

(54) RASPBERRY PLANT NAMED 'DIAMOND JUBILEE'

(50) Latin Name: ***Rubus ideaus* L**
Varietal Denomination: Diamond Jubilee

(71) Applicant: Berryworld Plus Ltd., Broxbourne, Hertfordshire (GB)

(72) Inventor: Peter Edward Vinson, Hernhill Faversham (GB)

(73) Assignee: Berryworld Plus Ltd., Hertfordshire (GB)

( * ) Notice: Subject to any disclaimer, the term of this patent is extended or adjusted under 35 U.S.C. 154(b) by 0 days.

(21) Appl. No.: 13/694,890

(22) Filed: Jan. 16, 2013

(65) Prior Publication Data

US 2013/0212755 P1 Aug. 15, 2013

(30) Foreign Application Priority Data

Feb. 13, 2012 (QZ) ..... PBR 20120339

(51) Int. Cl.
*A01H 5/00* (2006.01)

(52) U.S. Cl.
USPC ..... Plt./204

(58) Field of Classification Search
USPC ..... Plt./204
See application file for complete search history.

*Primary Examiner* — Anne Grunberg
(74) *Attorney, Agent, or Firm* — Rosenberg, Klein & Lee

(57) ABSTRACT

The present invention is a new and distinct double cropping red raspberry cultivar named 'Diamond Jubilee', which is capable of producing high yields of large, bright colored, sweet and exceptionally firm fruit that has positive consumer appeal characteristics. The cultivar is characterized by its high cane vigor, large leaves, its low acidity, sweetness and firmness and its fruit morphology, specifically its broad conical shape. 'Diamond Jubilee' plants are also outstanding in that they produce commercial quantities of large, firm and flavorful fruit with long postharvest life in both the overwintering floricanes and late summer primocanes.

12 Drawing Sheets

Genus and species: *Rubus ideaus* L.
Cultivar denomination: 'Diamond Jubilee'.

CROSS-REFERENCE TO RELATED APPLICATIONS

This invention claims priority under 35 U.S.C. §119(f) of application number 2012/0339 filed on 13 Feb. 2012 at the European Community Plant Variety Office (CPVO).

BACKGROUND OF THE INVENTION

This invention concerns a new and distinct cultivar of a double cropping raspberry plant with a botanical name of *Rubus ideaus* L. The new and distinct cultivar of the present invention is a raspberry plant named 'Diamond Jubilee'. The new cultivar is distinguished from other cultivars by its combination of fruit firmness, low acidity, large size, extended shelf life and productivity. 'Diamond Jubilee' is thereby suitable for premium fresh fruit marketing in commercial production areas worldwide.

DESCRIPTION OF RELATED PRIOR ART

A number of cultivars of raspberry plants are known. This new and distinct cultivar differs from other cultivars such as 'Marcianna' (U.S. Plant Pat. No. 21,007), Caroline (U.S. Plant Pat. No. 10,412), Joan Squire (unpatented) and Polka (unpatented) in bearing large broad conical bright red fruit, whereas 'Marcianna' (U.S. Plant Pat. No. 21,007) bears long conic medium red berries, Caroline (U.S. Plant Pat. No. 10,412) and Joan Squire (unpatented) bear smaller and slightly elongated fruit. Compared with 'Marcianna' (U.S.

Plant Pat. No. 21,007), 'Diamond Jubilee' produces more root and crown-suckers and has higher yield and fruit firmness than Polka or Joan Squire under UK growing conditions. 'Diamond Jubilee' can be distinguished from 'Marcianna' (U.S. Plant Pat. No. 21,007), Joan Squire (unpatented), Caroline (U.S. Plant Pat. No. 10,412) and Polka (unpatented) in that 'Diamond Jubilee' fruit is lighter colored, firmer and more cohesive, giving the fruit an outstanding shelf life. In the UK 'Diamond Jubilee' produces a floricane, or overwintered crop of similar yield to the primocane crop which is not usual with other varieties such as Caroline (U.S. Plant Pat. No. 10,412) and Polka (unpatented). 'Diamond Jubilee' fruit is more round, has less acid, less pubescent and is lighter colored when fully ripe, compared to the elongated slightly darker 'Marcianna' (U.S. Plant Pat. No. 21,007) fruit or the much darker slightly longer Polka (unpatented) fruit. 'Diamond Jubilee' plants are more upright and more vigorous with thicker cane diameter than 'Marcianna' (U.S. Plant Pat. No. 21,007), Caroline (U.S. Plant Pat. No. 10,412) or Joan Squire (unpatented) and produce fruit a few days later on primocanes than 'Marcianna' (U.S. Plant Pat. No. 21,007), Caroline (U.S. Plant Pat. No. 10,412) or Joan Squire (unpatented) but the start of cropping is similar to Josephine (U.S. Plant Pat. No. 12,173) under UK growing conditions. 'Diamond Jubilee' fruit is larger, firmer, milder in acid, much lighter colored and easier to remove from the plant than many other standard primocane varieties, including Caroline (U.S. Plant Pat. No. 10,412), Joan Squire (unpatented), Josephine (U.S. Plant Pat. No. 12,173). 'Diamond Jubilee' plants are more vigorous in the UK growing conditions than Joan Squire (unpatented) but it is similar to Polka (unpatented). 'Diamond Jubilee' produces a large floricane crop of similar fruit size as primocane fruit.

ORIGIN OF THE NEW CULTIVAR

This new invention presents a new and distinct double cropping red raspberry cultivar named 'Diamond Jubilee'. The new cultivar was selected as an open pollinated seedling in Faversham, UK in August 2009 as part of an ongoing breeding program. The family, designated as "BMR" was germinated in the winter of 2008 and grown at Faversham, Kent, United Kingdom. The seeds making up the BMR family originated from fruit purchased in a retail store. The exact origin of the purchased fruit is unknown but it is believed to have been fruit of the variety 'Driscoll Maravilla' (U.S. Plant Pat. No. 14,804). A number of seedlings were selected from the BMR family and given further trialing. Subsequently one seedling which has been identified as BMR-V1 demonstrated commercial potential. Within the breeders designation the 'B' represents the year of selection, the 'MR' represents the family code, the 'V' represents the location of the seedling field and 1 represents the selection number within the family. A detailed comparison of 'Diamond Jubilee' and 'Driscoll Maravilla' is set forth in the following chart.

| Characteristics | Diamond Jubilee | Driscoll Maravilla |
|---|---|---|
| Acidity | Very low | Not mentioned |
| Shelf life | 36 hours longer than Maravilla when chilled | Extended shelf life |
| Ease of harvest | Does not separate so readily from receptacle as Maravilla & on some occasion leaves a few druplets behind on receptacle | Separates easily from its receptacle |
| Ripening season - floricane crop | 2-3 days earlier than Maravilla under UK growing conditions | |
| Ripening season - primocane crop | 2 weeks earlier than Maravilla under Uk growing conditions | |
| Leaf colour - upper side | 137A | 147A |
| Leaf colour - under side | 138B & 191A | 148C & 148B |
| Petiole length (cm) | Pentafoliate 8.84, trifoliate 5.13 | 6.2, 7.6 (not mentioned which type of leaves) |
| Terminal leaflet - length (cm) | 15.25 | 13.25 |
| Terminal leaflet - width (cm) | 9.25 | 8.1 |
| Terminal leaflet tip | Apiculate | Acuminate |
| Terminal leaflet base | Cordate to truncate | Round to cordate |
| Lateral leaflet length - (cm) | 11.48 | 12.8 |
| Lateral leaflet width - (cm) | 8.64 | 8.35 |
| Flower diameter | 2.69 | 1.65 |
| Fruit colour - maturing | 41A | 46A |
| Fruit colour - mature | 44A | 46A, 59A |
| Fruit glossiness | Medium - high | Medium |
| Fruit shape | Broad conical | Ovate |
| Fruit size - length (cm) | 2.9 | 1.95 |
| Fruit size - width (cm) | 2.7 | 2 |
| Fruit - length:width ratio | 0.93 | 0.97 |
| Fruit weight - floricane fruit (g) | 6.8 | 5.5; 3.1 |
| Fruit weight - primocane fruit (g) | 9.2 (average primary berry weight) | 4.2; 2.2 |
| Number of drupelets | 189; 152 | 83; 72 |
| Anther number per flower | 73 | 86 |
| Soluble solids (Brix %) | 9.2 | 1.36, 1.58 |

'Diamond Jubilee' was produced asexually by tissue culture in Dundee, Scotland in 2011, 2012 and 2013 and by root cuttings in Faversham, Kent, UK in 2012 and 2013. All manners of asexual reproduction have shown the variety to be stable and true to type.

SUMMARY OF THE INVENTION

This application relates to a new and distinct red fruited, double cropping, raspberry cultivar, botanically known as *Rubus ideaus* L. The following characteristics are outstanding:

- Production of fruit which is very firm and dry, light colored, large and low in acid.
- In all the areas of test of this selection the fruit is larger and firmer than most primocane bearing cultivars and has an extended shelf life.
- 'Diamond Jubilee' canes are producing a spring and an autumn crop in the United Kingdom and in Spain where the fruit color, size and firmness is consistent.

With respect to the extended shelf life of 'Diamond Jubilee', shelf life comparisons were made in the UK and both varieties were exported from Spain. The following tables evidence the extended shelf life of 'Diamond Jubilee' as compared to the Maravilla Variety. Appearance, taste and texture scores were judged on a scale of 1-5.

'Diamond Jubilee' ("DJ") Chilled Punnet

| Day | Appearance | Taste | Texture | Total score | rots/ molds | other comments |
|---|---|---|---|---|---|---|
| 0 | 3 | 4 | 4 | 11 | — | bleeding and collapse + 1 bleed |
| 1 | 3 | 4 | 4 | 11 | — | |
| 2 | 3 | 2 | 2 | 7 | — | |
| 3 | 3 | 3 | 3 | 9 | — | |

'Diamond Jubilee' ("DJ") Ambient Punnet

| Day | Appearance | Taste | Texture | Total score | rots/ molds | other comments |
|---|---|---|---|---|---|---|
| 0 | 4 | 4 | 4 | 12 | — | |
| 1 | 4 | 4 | 4 | 12 | — | |
| 2 | 2 | 2 | 2 | 9 | — | |
| 3 | 2 | 3 | 2 | 9 | — | |

Maravilla Chilled Punnet

| Day | Appearance | Taste | Texture | Total score | rots/ molds | other comments |
|---|---|---|---|---|---|---|
| 0 | 3 | 4 | 4 | 11 | — | |
| 1 | 3 | 3 | 3 | 9 | — | |
| 2 | 2 | 2 | 3 | 7 | — | |
| 3 | 2 | 2 | 2 | 6 | 1 rot | |

Maravilla Ambient Punnet

| Day | Appearance | Taste | Texture | Total score | rots/ molds | other comments |
|---|---|---|---|---|---|---|
| 0 | 4 | 4 | 4 | 12 | — | |
| 1 | 4 | 3 | 4 | 11 | — | |
| 2 | 4 | 3 | 4 | 8 | — | |
| 3 | 3 | 3 | 3 | 7 | — | |

Summary

| Day | DJ chilled | DJ Ambient | Maravilla chilled | Maravilla ambient |
|---|---|---|---|---|
| 0 | 11 | 12 | 11 | 12 |
| 1 | 11 | 12 | 9 | 11 |
| 2 | 7 | 9 | 7 | 8 |
| 3 | 9 | 9 | 6 | 7 |

These characteristics make 'Diamond Jubilee' suitable as a late double cropping type for premium fresh fruit marketing in commercial production areas worldwide. In cooler areas with less than 2000 growing degree days, 'Diamond Jubilee' primocane fruit ripens from the beginning of August and through September and the floricane fruit ripens from mid-June through July.

Overwintered 'Diamond Jubilee' plants with floricanes in southern Spain produced sporadic bud break after mechanical defoliation and 250 chilling hours. This 50-60% bud break response is typical of a genotype which requires a moderate (approx. 600) amount of chilling hours.

'Diamond Jubilee' plants with primocanes, grown in pots for the summer crop and overwintered, produce sufficient quantities of large and firm fruit to be useful as a primocane and floricane double cropping cultivar in the UK. Floricane fruit production has not been tested in areas that experience very high chill and significant sub freezing temperatures, therefore, no claims are made concerning cold hardiness below −5° C.

The following characteristics are useful in distinguishing this cultivar from other cultivars and can be useful for cultivar identification. Plants used for these observations were grown under polythene tunnels in un-crowded conditions and in full sunlight.

1. When cane density is below 6 canes per meter of row on non-tissue culture propagated plants at least one year old, 'Diamond Jubilee' plants produce primocanes which terminate in flower clusters. 'Diamond Jubilee' canes usually produce flowers at the 21$^{st}$ node in the United Kingdom. By comparison, 'Marcianna' (U.S. Plant Pat. No. 21,007) produces fruit, on average, at the 24$^{th}$ node. Above the 21$^{st}$ node, an additional 15 nodes produce flower trusses; therefore an average of 44% well illuminated 'Diamond Jubilee' primocane produces flowers.
2. The initial or primary fruit is broad conical; nearly as wide as long with a ratio of width to length within 10% of 1 to 1. Primary 'Diamond Jubilee' fruit have a large receptacle cavity, with the cavity diameter comprising approximately 40% of the fruit width. Drupelets are more tightly adhered to each other than 'Marcianna' (U.S. Plant Pat. No. 21,007). Upon full ripening the fruit retains its bright glossy appearance compared to 'Marcianna' (U.S. Plant Pat. No. 21,007) in which a few drupelets may develop a slight darker coloration under the attachment of the remnant pistil.
3. Thorns are moderately numerous, averaging at 12 thorns per 6 cm internode length measured at 30 cm height from the top of the plant. At the base, however thorns have been found in slightly greater abundance, as typical of the species, averaging at 27.3 thorns per 4.5 cm internode length, measured at 30 cm height from the base of the plant.

The coloration and shape of the thorns on primocanes is typical of 'Diamond Jubilee' and can be used to distinguish the new cultivar from some other cultivars. Thorn coloration is consistently Greyed-purple (1995 Royal Horticultural Society Colour Chart, Greyed-purple group 183A) and the coloration extends about 0.1-0.4 mm around the base into the surrounding cane. The shape of the extension of color into the cane is generally round, however some larger thorns might exhibit an oval shape that is longitudinal to the axis. Thorns are generally 1-1.5 mm in length, relatively thick and straight, pointy and needle-like.

4. The colors of the petioles and leaf veins are of The 1995 Royal Horticultural Society Colour Chart, Yellow-green group No 144B. When plants are grown in non-crowded conditions with adequate fertilization and irrigation, leaves are primarily pentafoliate at the base of the primocane, but are mostly trifoliate primarily in the floral cane area. The color of the underside of the trifoliate leaves (1995 Royal Horticultural Society Colour Chart, Green group No. 138 B) is slightly different to the underside of the pentafoliate leaves (1995 Royal Horticultural Society Colour Chart, Greyed-green group No. 191 A). The upper surface color of pentafoliate and trifoliate leaves is similar however (1995 Royal Horticultural Society Colour Chart, Green group No. 137A).

BRIEF DESCRIPTION OF THE PHOTOGRAPHS

The accompanying color photographs show typical specimens of the new cultivar, designated at various stages of development as nearly true as is possible to make in color reproductions. The depicted plant and plant parts were from the 2012 harvest season grown under polythene tunnels in Kent, UK.

Figure 12:
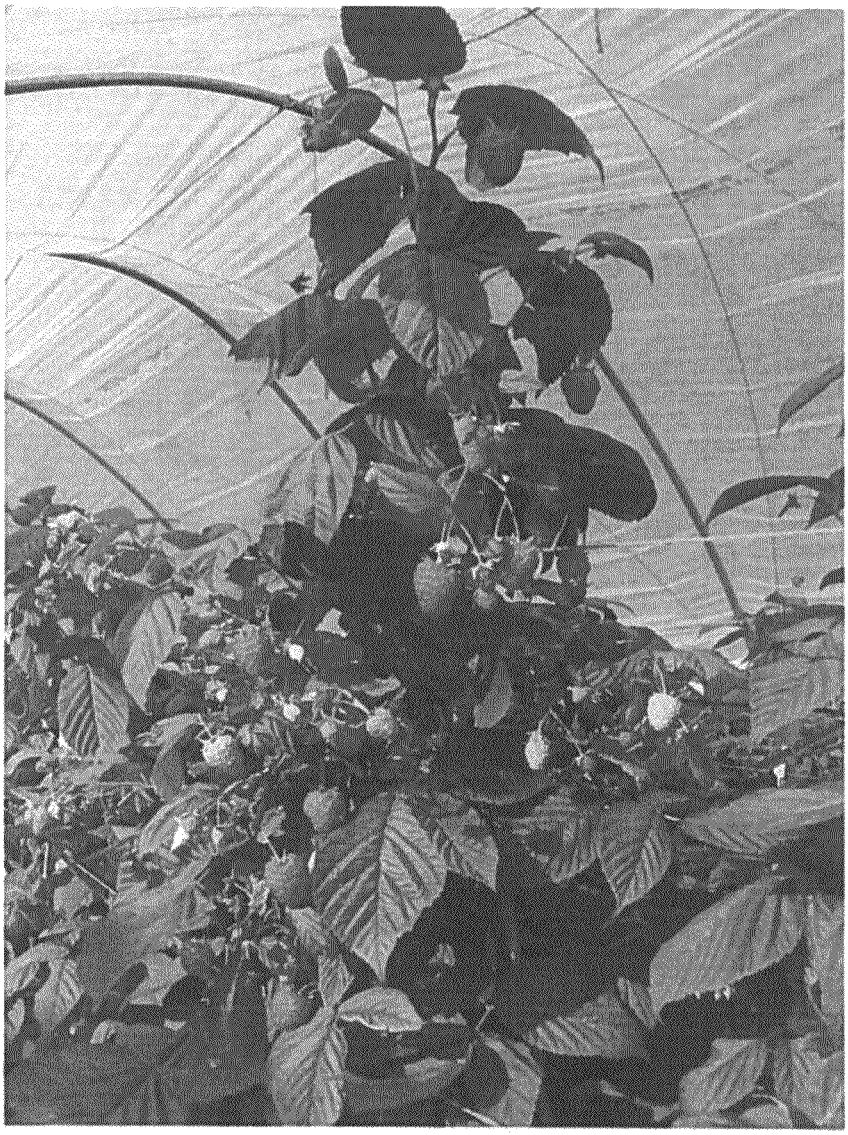

FIG. 12 Photo of a primocane fruiting cluster of 'Diamond Jubilee' in mid August.

Figure 13:
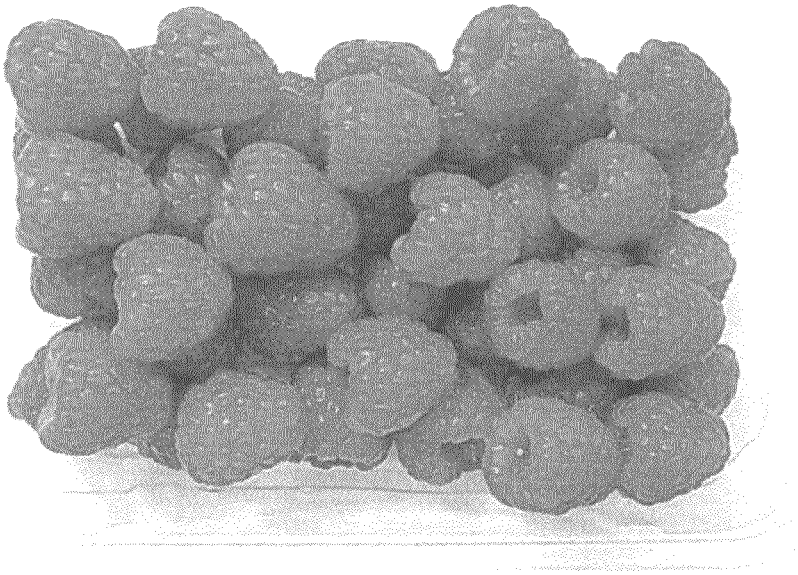

FIG. 13 Shows the initial primocane fruit of 'Diamond Jubilee' as it would occur in a market.

DETAILED BOTANICAL DESCRIPTION OF THE NEW CULTIVAR

The following is a detailed description of 'Diamond Jubilee', the new cultivar, including fruit production, together with the cultivar's morphological characteristics. 'Diamond Jubilee' is a species hybrid, which contains a predominance of *Rubus ideaus* L traits and would be botanically classified in that species commonly referred to as red raspberries. The characteristics of the cultivar were compared with other standards used in the United Kingdom and Spain. The description is based on information and observation provided by cooperating growers from trials plants grown in fields at Faversham, Kent, England; Wokingham, Berks, England and Cartaya, Spain. As these climates differ, particularly in temperatures experienced in the growing season, it is believed that the description of 'Diamond Jubilee' will be consistent in other locations.

Figure 8:
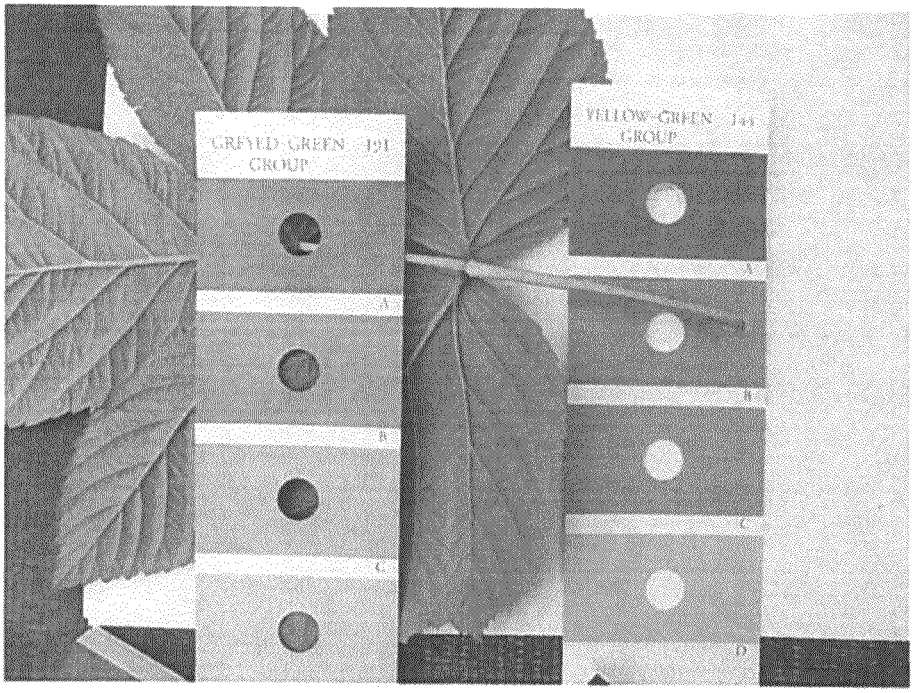
FIG. 8 Shows a lower leaf surface color identification of a fully expanded pentafoliate 'Diamond Jubilee' leaf using The 1995 Royal Horticultural Society Colour Chart (191A) and petiole color identification using The 1995 Royal Horticultural Society Colour Chart (144B).
Figure 9:
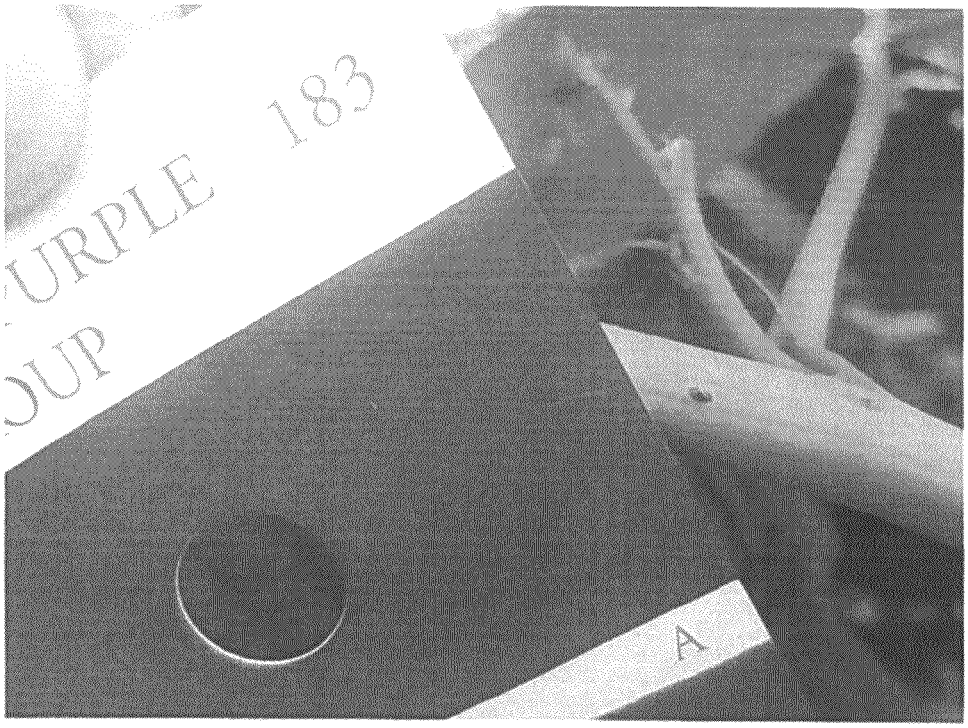
FIG. 9 Shows a density and color of thorns of 'Diamond Jubilee' canes identified using The 1995 Royal Horticultural Society Colour Chart (183A).
Figure 10A:
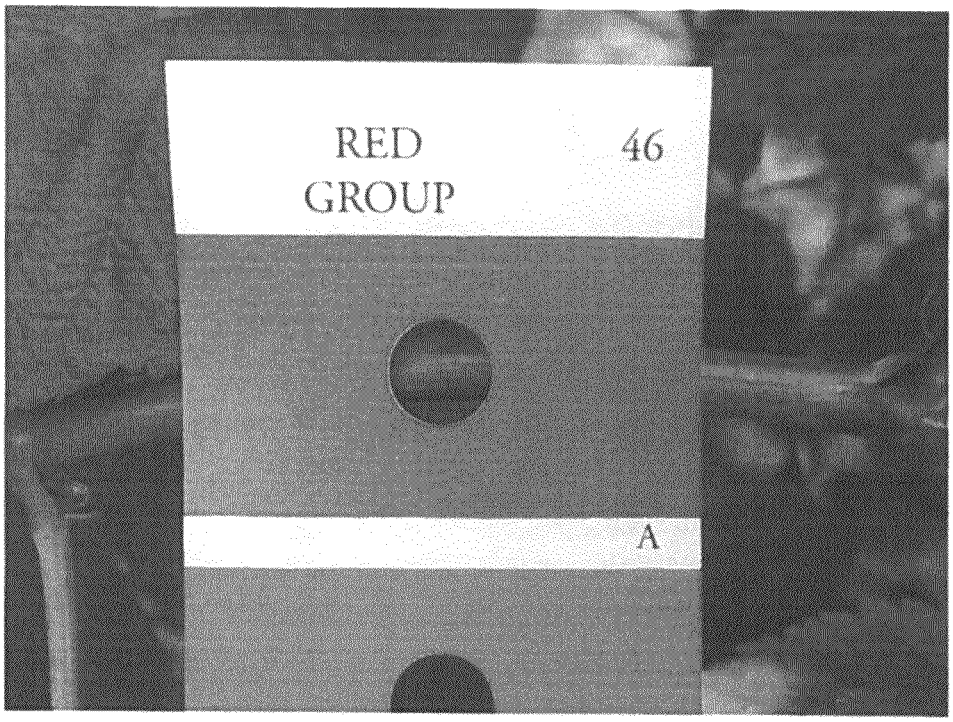
FIGS. 10A, 10B, 10C and 10D shows photos of primocanes anthocyanin coloration late in the season, identified using The 1995 Royal Horticultural Society Colour Chart (46A, 47B, 48D and 60A).
Figure 10B:
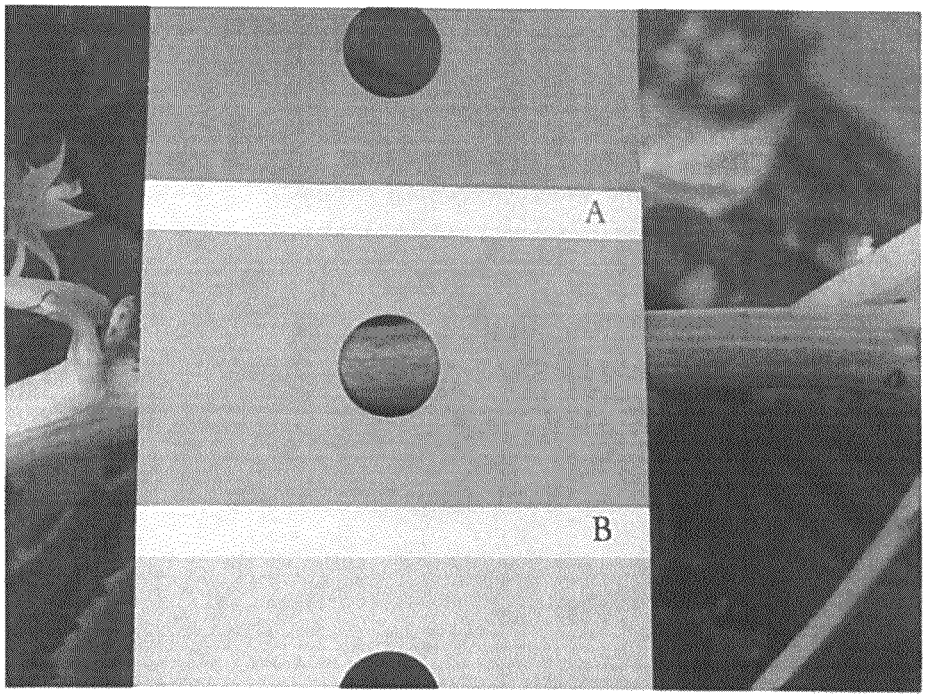
Figure 10C:
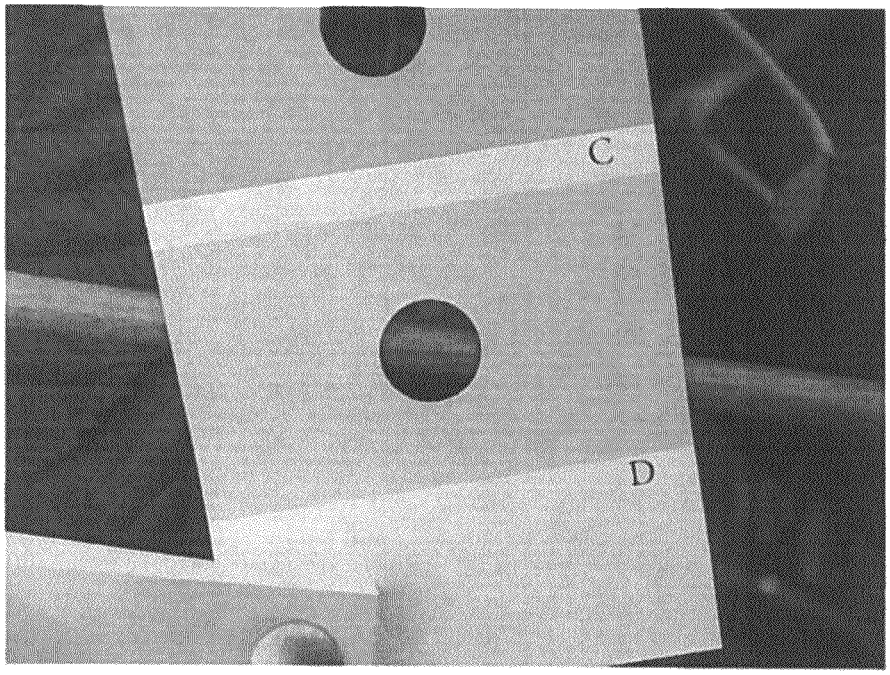
Figure 10D:
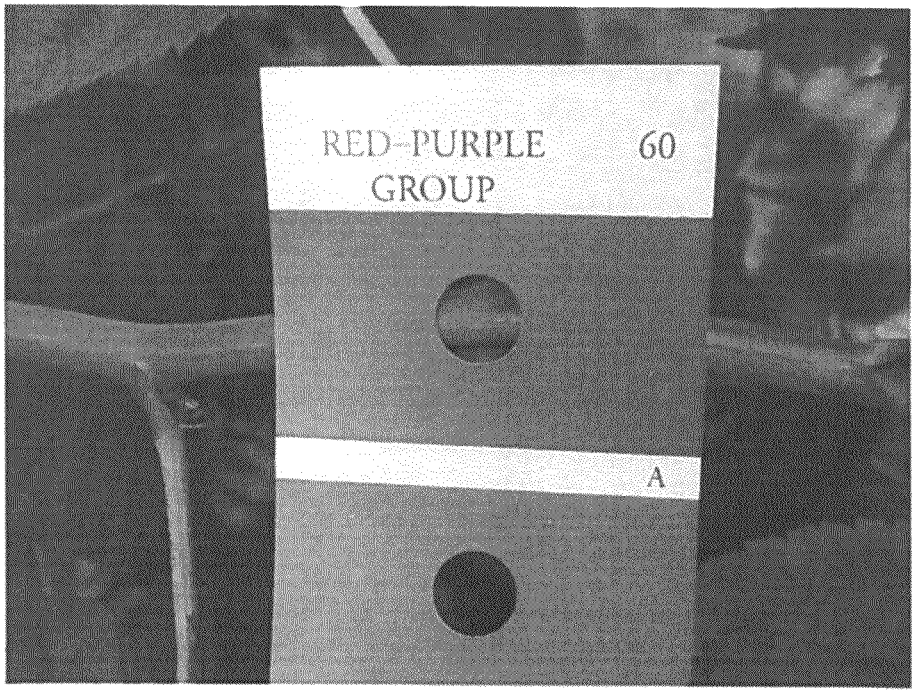
Figure 11:
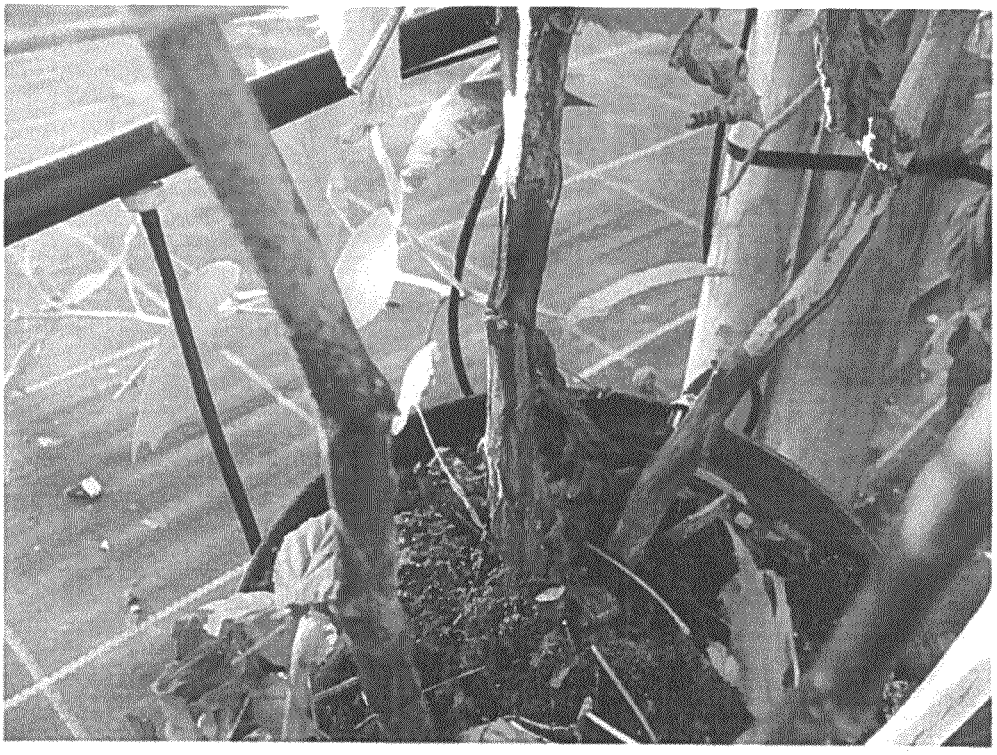
FIG. 11 Shows the base of a mature floricane in mid-November and the pattern of slight exfoliation of the bark and 1995 Royal Horticultural Society Colour Chart (175A).

'Diamond Jubilee' produces a moderate to high number of root- and crown-suckers ranging from 15-20 per plant. During the growing season canes are light green colored (1995 Royal Horticultural Society Colour Chart, Yellow-green group, 144B) (FIG. 8). Towards the end of the season, paired with lower temperatures, canes exhibit a red blush, with variable color intensity identified by using The 1995 Royal Horticultural Society Colour Chart as Red-group 46A, 47B and 48D (FIGS. 10A, 10B and 10C) and Red-purple group 60A (FIG. 10D) on approximately 10% of the cane exposed to full sunlight. Canes are usually erect and branched by the second year of a plant's growth. Total node number per cane is approximately 35 for second year adult, non-tissue culture plants, whereas 'Marcianna' (U.S. Plant Pat. No. 21,007) produces 40 nodes per cane as a second year non-tissue culture plant. Growth is vigorous, reaching on average 156 cm in full sun in un-crowded conditions in tunnels in the UK, measured on 17 Jul. 2012. The length of internodes at 30 cm above ground in well lighted plants is 4.5 cm compared to 'Marcianna' (U.S. Plant Pat. No. 21,007) that has 4.75 cm long internodes grown under similar conditions. Cane diameter at the same location measures 1.1 cm, whereas 'Marcianna' (U.S. Plant Pat. No. 21,007) measures 1 cm.

Thorns are moderate in density at the base of the canes, ranging from 17 to 29 per internode. At the apex of the canes the number of thorns average at 12. Thorn shape is straight and needle-like and length is approximately 1-1.5 mm, similar to 'Marcianna' (U.S. Plant Pat. No. 21,007). 'Diamond Jubilee' thorn color is Greyed-purple (1995 Royal Horticultural Society Colour Chart, 183A) in color throughout; including 0.3 mm of the surrounding epidermis of the cane. The thorn coloration of the cane exhibits both round and oval orientation with the long axis parallel to the axis of the cane. The color of the thorns turns brown in the dormant season, matching that of the overwintering floricanes, a similar pattern of coloration occurs with lateral buds, which are typical in size and shape of the species.

Figure 7:
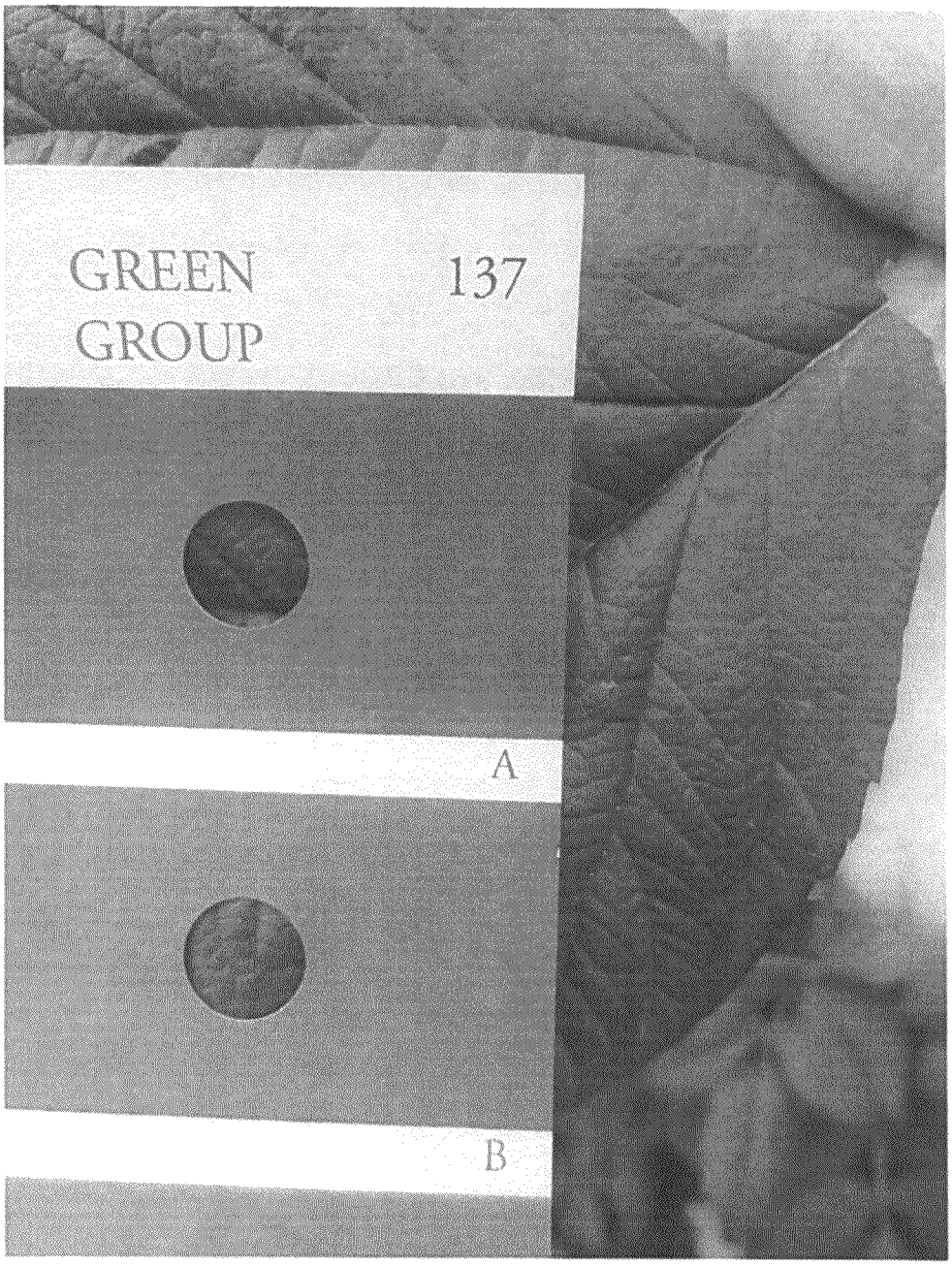
FIG. 7 Shows an upper leaf surface color identification of a fully expanded pentafoliate leaf of 'Diamond Jubilee', using The 1995 Royal Horticultural Society Colour Chart (137A).

The pubescence of the lower surface of trifoliate and pentafoliate 'Diamond Jubilee' leaves is very fine and short, not immediately obviously observed. The lower surface of trifoliate and pentafoliate 'Diamond Jubilee' leaves have been identified by using The 1995 Royal Horticultural Society Colour Chart as Green group 138 B and Greyed-green group 191 A (FIG. 8) respectively. The upper surfaces of both pentafoliate and trifoliate leaves are similar dark green most closely identified using The 1995 Royal Horticultural Society Colour Chart, Green group 137A (FIG. 7), depending on the time of season. Senescing leaves have a Yellow-green color resembling 1995 Royal Horticultural Society Colour Chart 151 A-B and 145 A-B. Vigorous plants have leaves that are 90% pentafoliate at nodes 1 to 18. Above node 22 only trifoliate leaves occur. The pentafoliate terminal leaflet is averaging at 15.25 cm in length and 9.25 cm in width. The trifoliolate terminal leaflet measures 6.6 cm in width and 4.5 cm in length.

The pentafoliate maximum leaf width measured from the apex of a lateral leaflet to the opposite lateral leaflet apex is, on average, 26.65 cm whereas 'Marcianna' (U.S. Plant Pat. No. 21,007) measures 22.86 cm. The trifoliate maximum leaf width, measured from the apex of the lateral leaflet to the opposite lateral leaflet apex is, on average, 24.8 cm compared to 'Marcianna' (U.S. Plant Pat. No. 21,007) that measures 18.52 cm. The pentafoliate leaf petiole, basal petiolule and apical petiolule lengths averages 8.84 cm, 4.83 cm and 2.13 cm respectively for a total of 15.8 cm. By comparison 'Marcianna' (U.S. Plant Pat. No. 21,007) measures 7.64 cm, 4.58 cm and 2.38 cm respectively for a total of 14.6 cm. The trifoliate leaf petiole length averaged 5.13 cm and terminal petiolule length averaged 3.38 cm, compared to 'Marcianna' (U.S. Plant Pat. No. 21,007) averaging 5.08 cm and 3.08 cm respectively. Lateral leaflets are sessile where they join the petiole. Leaf serration, moderate laminar puckering and venation pattern are common for most cultivars of red raspberry and cannot be used to distinguish this cultivar.

In the UK leaves abscise readily in October and November and coloration changes. 'Diamond Jubilee' canes are slightly blotchy orange brown in color, resembling in hue The 1995 Royal Horticultural Society Colour Chart, Greyed-orange group 175 A and B for the dark brown patches and The 1995 Royal Horticultural Society Colour Chart 166A and 166B for the lighter Greyed-orange brown patches. Floricanes exfoliate to a moderate amount mainly at the base of the canes.

Flowers appear after the 21$^{st}$ node, on average, on adult 'Diamond Jubilee' primocane plants. By comparison, adult 'Marcianna' (U.S. Plant Pat. No. 21,007) primocanes flower, on average, after the 24$^{th}$ node. Fruit appears on 15 nodes on average whereas on 'Marcianna' (U.S. Plant Pat. No. 21,007) plants this occurs on 16 nodes on average. Fruit is borne on 44% of the total nodes of the primocanes. The proportion of cane producing primocane fruit is slightly less than 'Marcianna' (U.S. Plant Pat. No. 21,007), however 'Diamond Jubilee' primocane yields are approximately 50% higher than 'Marcianna' (U.S. Plant Pat. No. 21,007).

Figure 4:
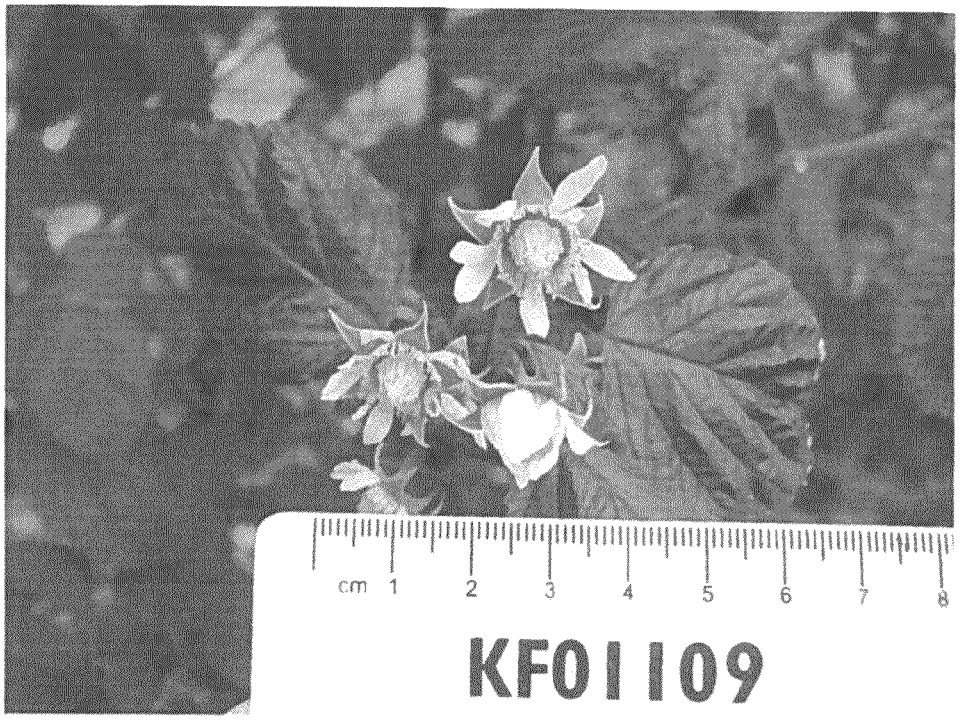
FIG. 4 Shows a typical 'Diamond Jubilee' flower with visible flower parts identified using The 1995 Royal Horticulture Society Colour Chart (155D).
Figure 5:
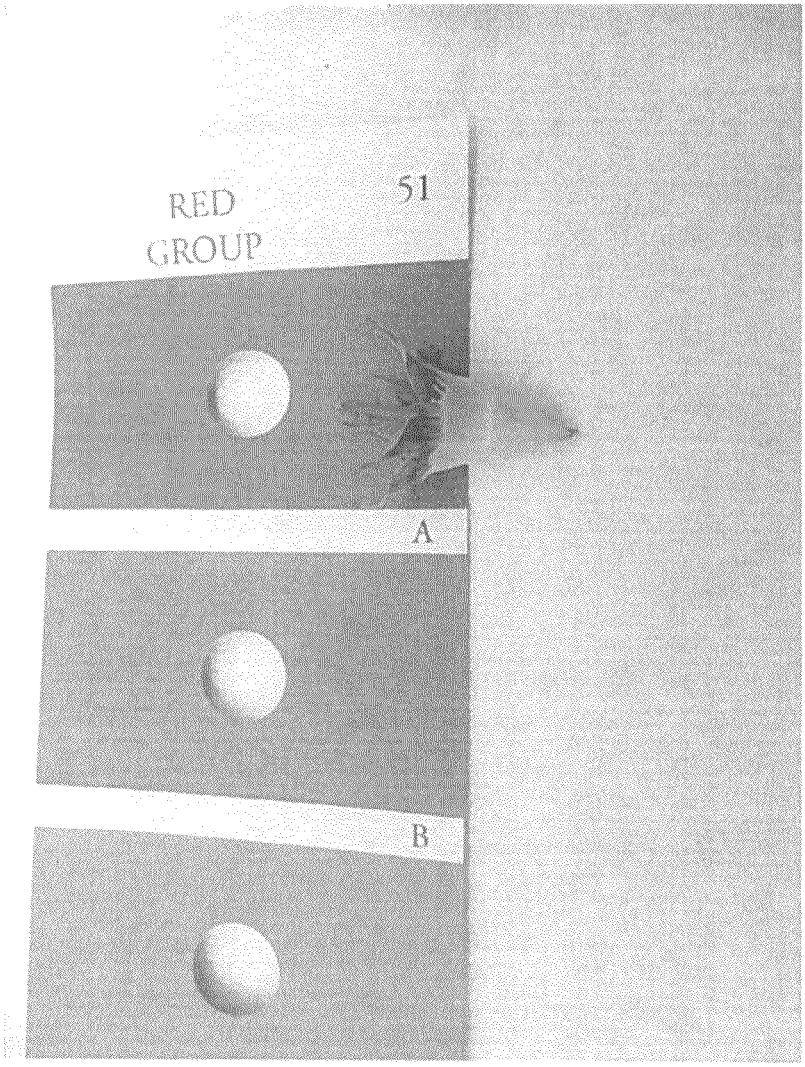
FIG. 5 Shows a typical primocane flower with the abaxial calyx expressing anthocyanin coloration, identified using The 1995 Royal Horticultural Society Colour Chart (51A).
Figure 6A:
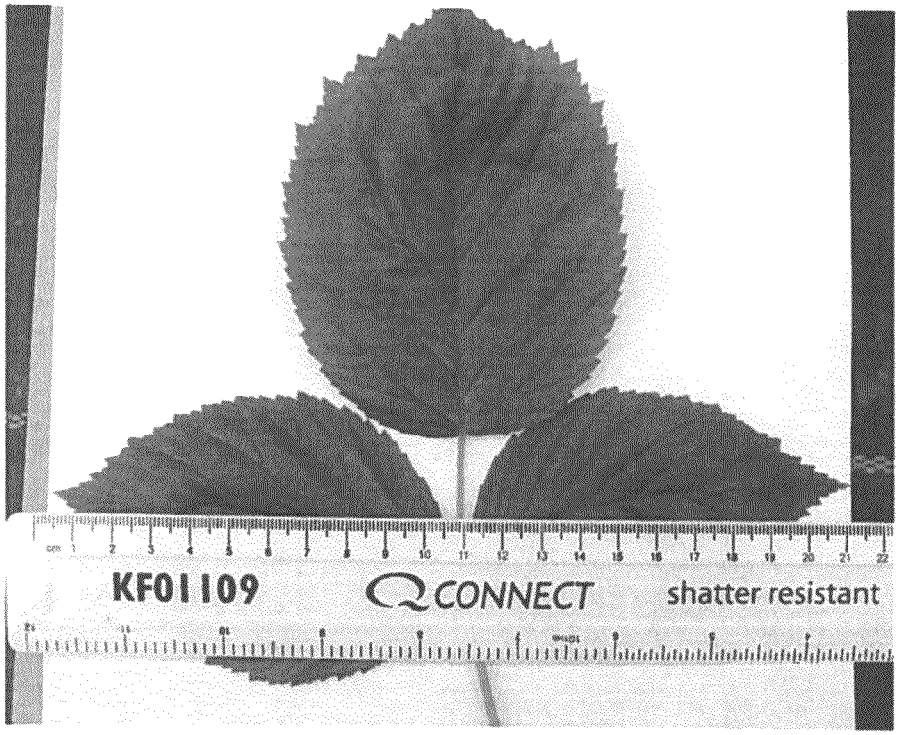
FIG. 6A Shows a typical mature trifoliate leaf measured in length and width showing pointy serrations and channel-like venations.
Figure 6B:
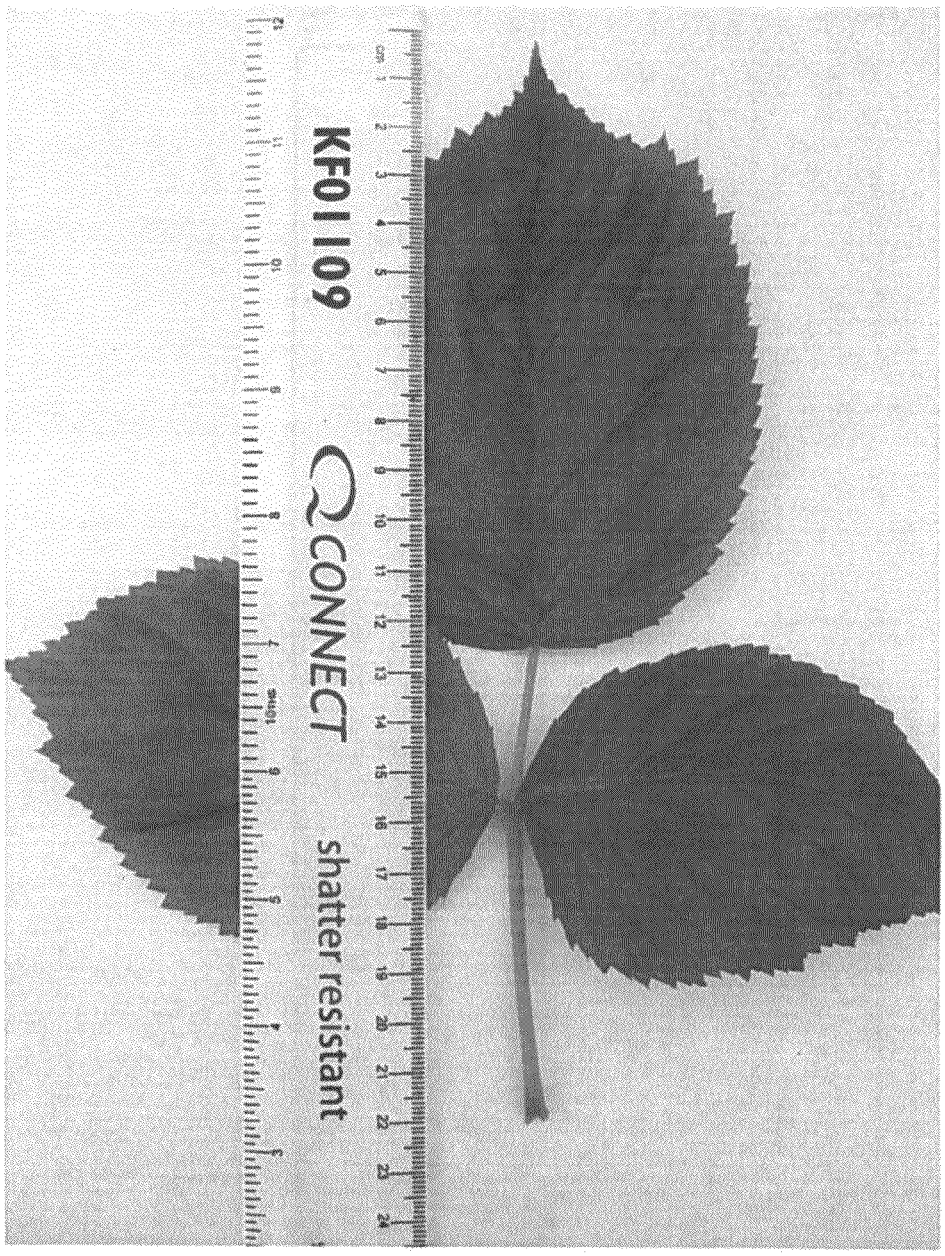
FIG. 6B Shows a typical mature trifoliate leaf measured in width showing pointy serrations and channel like vanations.

The unscented flower morphology and early fruit morphology is typical of most red raspberry cultivars, having five white (1995 Royal Horticultural Society Colour Chart, White group 155D) petals that average 0.9 cm in length and 0.4 cm in width. Petals abscise after pollination. The flowers have five grey green sepals, rarely six, 1.5 cm long and 0.6 cm wide at the base, color identified using The 1995 Royal Horticultural Society Colour Chart, Greyed-green group, 191A (FIG. 4). Sepals are generally longer on primary flowers and slightly shorter on mid-season flowers and in the case of 'Diamond Jubilee' they lack heavy or long pubescence. The sepals of green 'Diamond Jubilee' fruit have no blush, however all sepals exhibit a narrow white edging from base to apex, color identified using The 1995 Royal Horticultural Society Colour Chart, White group 155D. As the fruit matures the abaxial side of the calyx develop an anthocyanin coloration with variable intensity, color identified using The 1995 Royal Horticultural Society Colour Chart as Red Group 51 A (FIG. 5) and Red Group 54 A. On the adaxial side of the calyx two occasionally three, of the sepals exhibit the same coloration, whereas the rest of the sepals present no anthocyanin coloration except approximately 10% which show a narrow edge colored identified using The 1995 Royal Horticultural Colour Chart as Red group 54 A.

Flowers have on average 94.6 pistils on primary fruit and an average of 84.6 anthers. The flowers of mid-season fruit is slightly smaller where pistils average at 76.4 and anthers average at 64.8. None of these traits can be used in confidence to identify 'Diamond Jubilee' from other known varieties. Flower trusses are typical simple cymose clusters. The total number of flowers per cane average at 111.6 on well lighted un-crowded canes. A small reduction in flower numbers per cane occurs on crowded canes averaging at 108.3.

The initial or primary fruits are easily distinguishable by their broad conical shape at approximately 12 days post pollination. When ripe these large fruits have an average sized receptacle cavity of about 1.1 cm in diameter. As these fruits are relatively wide, 2.7 cm in diameter, the receptacle cavity is approximately 40% of the fruit diameter, compared to 50% of the long conic fruited 'Marcianna' (U.S. Plant Pat. No. 21,007). The initial mature fruit length is 2.9 cm, producing an initial fruit width to length ratio of 0.95. This ratio can be used confidently to distinguish 'Diamond Jubilee' from other varieties known. The primary fruit on primocanes of 'Diamond Jubilee' have an average of 189 drupelets and an average weight of 9.2 g compared to 'Marcianna' (U.S. Plant Pat. No. 21,007) that bears primary fruit with an average of 105 drupelets and 5.5 g fresh weight. Mid-season fruit of 'Diamond Jubilee' are smaller averaging 152 drupelets resulting in a relatively small variation in fruit size over the season. 'Diamond Jubilee' fruit are cohesive and when picked fully ripe it separates easily from its receptacle. The fruit will not tear across the drupelets before individual drupelets separate from each other. Unless pollination problems exist, the fruit does not shatter under pressure of hand harvest.

Fruit ripens 31 days after pollination on floricanes and 33 days after pollination on primocanes in Faversham, Kent, UK. Under polythene tunnels floricane fruit starts to ripen during the last week of June and continues cropping through July in Kent where the 50% ripe date occurs on 12$^{th}$ July. Primocane fruit starts to ripen during mid August and continues cropping into mid October where in 2012 the 50% ripe date occurred on 7$^{th}$ September. Plants grown in Wokingham, Berkshire expressed a slightly earlier cropping profile where the primocane fruit picking started week commencing 6$^{th}$ August and terminated towards the end of October. Here the 50% ripe date occurred on 2$^{nd}$ September.

Figure 1:
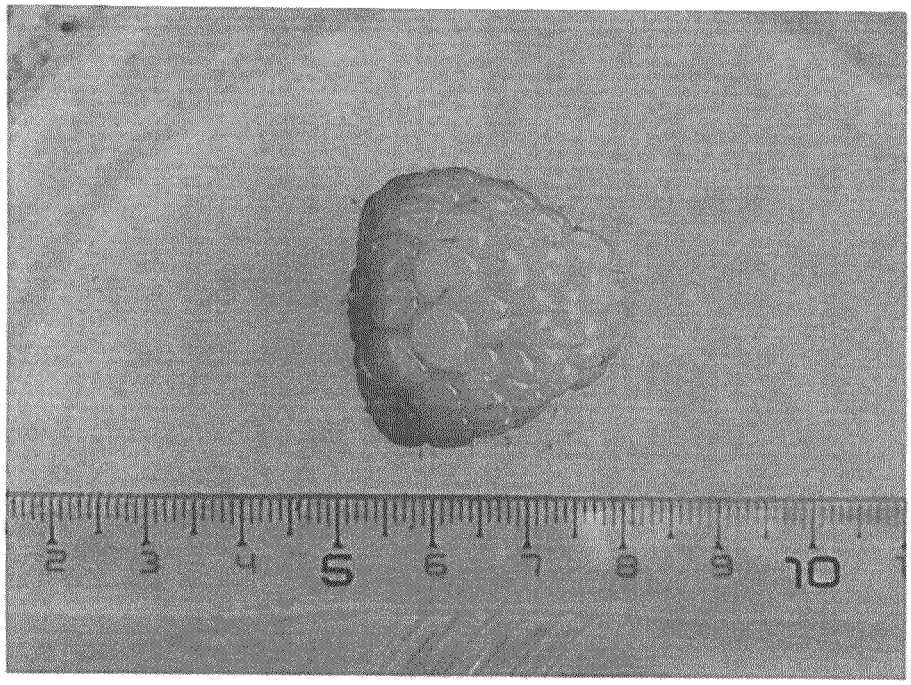
FIG. 1 Shows a typical fully developed primocane fruit measured in length (cm) identified using The 1995 Royal Horticulture Society Colour Chart (44A).
Figure 2:
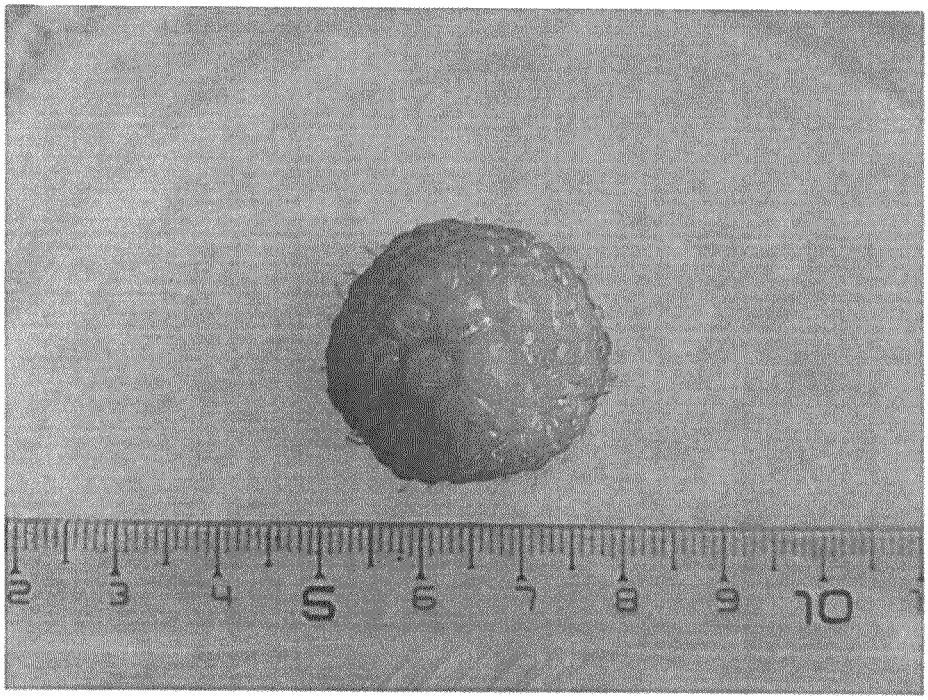
FIG. 2 Shows a typical l fully developed primocane fruit measured in width (cm) identified using The 1995 Royal Horticulture Society Colour Chart (44A).
Figure 3:
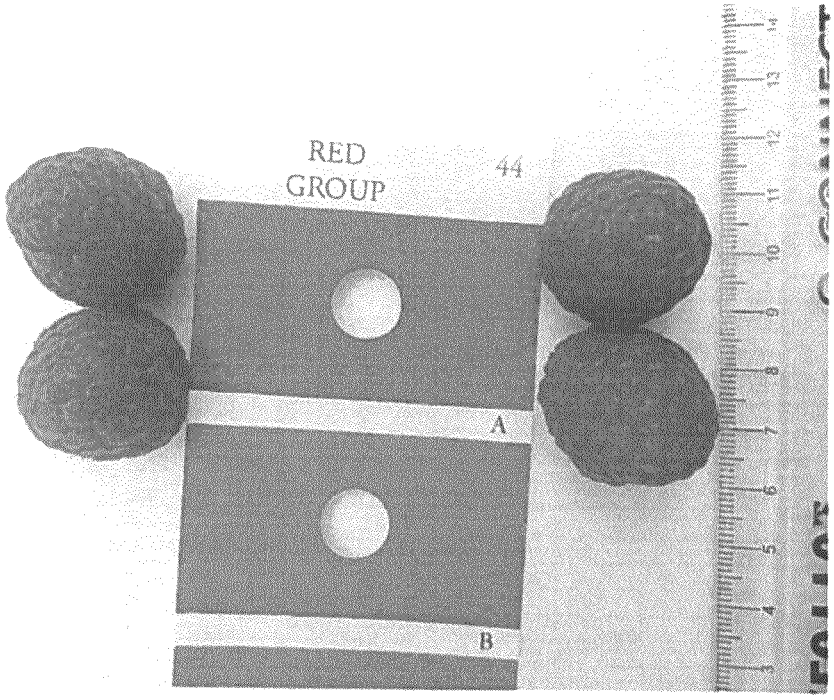
FIG. 3 Shows a typical color and shape of a mature primary fruit, identified using The 1995 Royal Horticultural Society Colour Chart (44A).

'Diamond Jubilee' fruit are medium red when fully ripe, closely resembling the hue of 1995 Royal Horticultural Society Colour Chart, Red group 44 A (FIG. 3) and slightly lighter color when maturing, resembling 1995 Royal Horticultural Society Colour Chart, Red group 41 A. The immature fruit color is closely resembling The 1995 Royal Horticultural Society Colour Chart, Yellow Green group, 151 A. When fully or over ripe, or upon 7 days cold storage, fruit retains its medium red color, resembling The 1995 Royal Horticultural Society Colour Chart Red group 44 A (FIG. 3). Fruits do not have a noticeable pubescence, a feature that is typical of most other commercial cultivars. The fruit readily separates from the plant's receptacle in warm conditions, but is slightly more difficult to remove when ripened in colder weather (<15C).

The variety is distinguishable by its extreme firmness which even after a period of cold storage results in minimal bleed at the point of sale of fresh fruit. The fruit does not break down after 7 days in cold storage at 4C. Flavour of 'Diamond Jubilee' is sweet with an average of 12.75% Brix for 6 consecutive weeks on primocane fruit in UK growing conditions, it is dry with low acid and is characteristic of red raspberry. Spring ripened fruit was rated above 'Tulameen' (Unpatented), 'Driscoll Maravilla' (U.S. Plant Pat. No. 14,804), and 'Glen Ample' (U.S. Plant Pat. No. 11,418) by a professional taste panel in the United Kingdom. The texture of the fruit is firmer than many other red raspberry cultivars known including 'Marcianna' (U.S. Plant Pat. No. 21,007), with the exception of 'Driscoll Maravilla' (U.S. Plant Pat. No. 14,804), a primocane fruiter with similar firmness.

FRUIT PRODUCTION

'Diamond Jubilee' has been tested in small scale trials in Kent and in Berkshire in the United Kingdom and in Cartaya, Spain. The following data were collected in the autumn of 2011 and summer and autumn of 2012. In Kent the plants were potted in 7.5 L pots in the summer of 2010 for the 2011 primocane yield data with the plants remaining in position for the floricane yield assessment in 2012. A second plot of 8 plants was potted in 7.5 L pots in the summer of 2011 for the assessment of primocane fruit in 2012. The data below could be classified as a normal yield for potted plant production under polythene tunnels. Total 2011 primocane yield of 'Diamond Jubilee' on potted plants grown in tunnels was 1828 g/pot with 4 canes in a pot. The same plants produced a total 2012 floricane yield of 2040 g/pot. In comparison 'Marcianna' (U.S. Plant Pat. No. 21,007) grown in the same location produced a primocane yield of 1154 g/pot. The total 2012 primocane yield from a second plot of 'Diamond Jubilee' grown in Faversham, Kent on potted plants amounted to 1625 g/pot whereas 'Marcianna' (U.S. Plant Pat. No. 21,007) yielded 953 g/pot. Plants of 'Diamond Jubilee' grown in Berkshire in 2012 produced a total primocane crop of 1764.1 g/pot.

Trials in Cartaya, Spain were only observational trials, no yield has been recorded.

DISEASE AND PEST RESISTANCE

'Diamond Jubilee' plant is moderately susceptible to two spotted spider mite. The plant did not exhibit any signs of raspberry root rot (*Phyophthora*), based on subjective observation, but insufficient testing has taken place to make any claims regarding resistance to this disease. Fruit is usually free from rot or botrytis in the polythene tunnels, more so than 'Marcianna' (U.S. Plant Pat. No. 21,007) and post-harvest fruit rot resistance appears to be better than many other commercial varieties. Resistance to powdery mildew is unknown, although no symptoms have been observed to date.

Propagation using in vitro culture, root cuttings and root sucker division has given consistent results whereby all stocks of 'Diamond Jubilee' have shown to be stable and exhibiting the distinguishing characteristics during four years of propagation.

What is claimed is:

1. A new and distinct double cropping red raspberry plant known as 'Diamond Jubilee' as described and illustrated herein, identified by the characteristics set forth above.

* * * * *